US012609194B2

(12) United States Patent
Kim et al.

(10) Patent No.: US 12,609,194 B2
(45) Date of Patent: Apr. 21, 2026

(54) MEDICAL IMAGE PROCESSING METHOD

(71) Applicant: VUNO Inc., Seoul (KR)

(72) Inventors: Byung Mook Kim, Seoul (KR);
Beomhee Park, Seoul (KR); Jonghoon Park, Seoul (KR)

(73) Assignee: VUNO INC., Seoul (KR)

( * ) Notice: Subject to any disclaimer, the term of this patent is extended or adjusted under 35 U.S.C. 154(b) by 318 days.

(21) Appl. No.: 18/553,186

(22) PCT Filed: Oct. 14, 2021

(86) PCT No.: PCT/KR2021/014186
§ 371 (c)(1),
(2) Date: Sep. 28, 2023

(87) PCT Pub. No.: WO2022/211195
PCT Pub. Date: Oct. 6, 2022

(65) Prior Publication Data
US 2024/0203566 A1    Jun. 20, 2024

(30) Foreign Application Priority Data

Apr. 1, 2021    (KR) ........................ 10-2021-0042510

(51) Int. Cl.
G06T 7/90        (2017.01)
G06T 5/40        (2006.01)
(Continued)

(52) U.S. Cl.
CPC .............. G16H 30/40 (2018.01); G06T 5/40 (2013.01); G06T 7/90 (2017.01); G06V 10/25 (2022.01);
(Continued)

(58) Field of Classification Search
CPC .......... G16H 30/40; G16H 50/20; G06T 5/40; G06T 7/90; G06T 2207/10024;
(Continued)

(56) References Cited

U.S. PATENT DOCUMENTS 9,092,691 B1 *  7/2015  Beaumont .............. G06V 10/25
10,383,602 B2   8/2019  Cho et al.
(Continued)

FOREIGN PATENT DOCUMENTS

JP        2012221365 A    11/2012
JP          5248120 B2    7/2013
(Continued)

OTHER PUBLICATIONS

Dikici et al., "Integrating AI into radiology workflow: levels of research, production, and feedback maturity," Journal of Medical Imaging, Feb. 11, 2020 (13 pages).

*Primary Examiner* — Ali Bayat
(74) *Attorney, Agent, or Firm* — Seed Intellectual Property Law Group LLP

(57) ABSTRACT

According to an exemplary embodiment of the present disclosure, a medical image processing method performed by a computing device is disclosed. The medical image processing method includes: detecting a region of interest in a medical image by using a pre-trained deep learning model; determining contour information for the region of interest; and generating, based on the contour information, format information defining elements that determine representation of the medical image.

20 Claims, 10 Drawing Sheets

(51) Int. Cl.
| | |
|---|---|
| *G06V 10/25* | (2022.01) |
| *G06V 10/46* | (2022.01) |
| *G06V 10/56* | (2022.01) |
| *G06V 10/60* | (2022.01) |
| *G16H 30/40* | (2018.01) |

(52) U.S. Cl.
CPC .............. *G06V 10/46* (2022.01); *G06V 10/56* (2022.01); *G06V 10/60* (2022.01); *G06T 2207/10024* (2013.01)

(58) Field of Classification Search
CPC   G06T 7/00; G06T 3/40; G06T 7/0012; G06T 7/11; G06T 2210/41; G06V 10/25; G06V 10/46; G06V 10/56; G06V 10/60; G06V 2201/03; G06V 10/24; G06N 3/0455; G06N 3/0464; G06N 3/09; G06N 3/08; A61B 5/00; A61B 5/055; A61B 6/00; A61B 6/03; A61B 5/0033; A61B 6/032; A61B 6/5217
USPC ........................................................ 382/128
See application file for complete search history.

(56) References Cited

U.S. PATENT DOCUMENTS

| | | | | |
|---|---|---|---|---|
| 10,592,743 | B2 * | 3/2020 | Borrel .................... | G06V 20/00 |
| 10,790,056 | B1 * | 9/2020 | Accomazzi ........... | G06T 11/008 |
| 2005/0034178 | A1 * | 2/2005 | Lee ........................ | C07K 14/47 |
| | | | | 514/44 R |
| 2013/0114740 | A1 * | 5/2013 | Kobayashi ............. | H04N 19/59 |
| | | | | 375/240.01 |
| 2017/0084028 | A1 * | 3/2017 | Vilsmeier ............... | G06T 15/20 |
| 2018/0342078 | A1 * | 11/2018 | Watanabe ........... | G06V 10/255 |
| 2021/0090247 | A1 * | 3/2021 | Jeon ....................... | G06V 10/82 |

FOREIGN PATENT DOCUMENTS

| | | | |
|---|---|---|---|
| KR | 10-2013-0058972 | A | 6/2013 |
| KR | 10-2015-0108701 | A | 9/2015 |
| KR | 101716039 | B1 | 3/2017 |
| KR | 102108401 | B1 | 5/2020 |

* cited by examiner

[Figure 1]
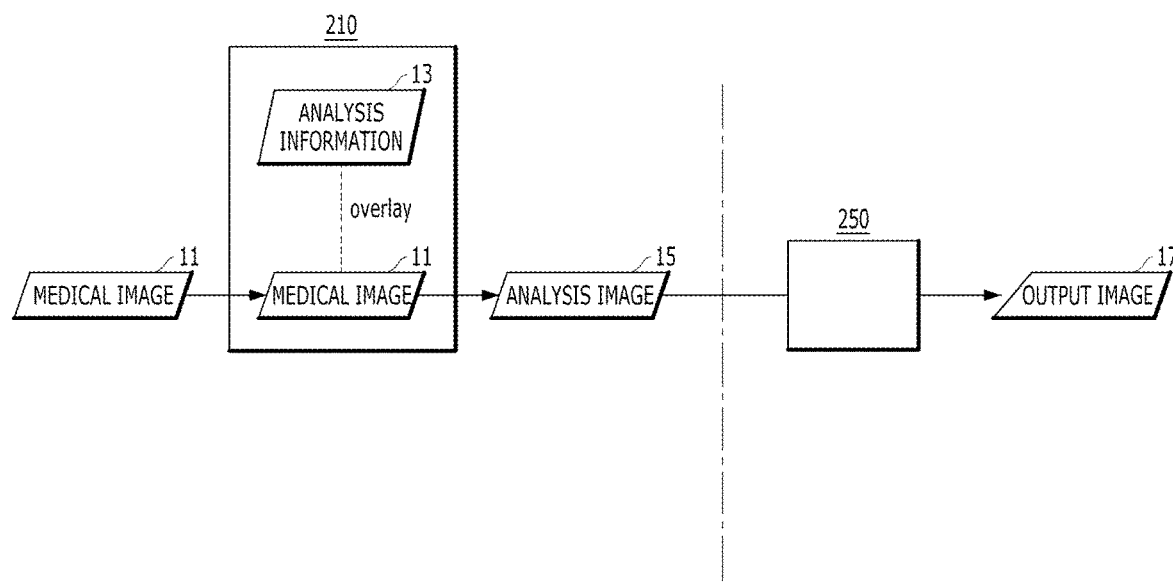

[Figure 2]
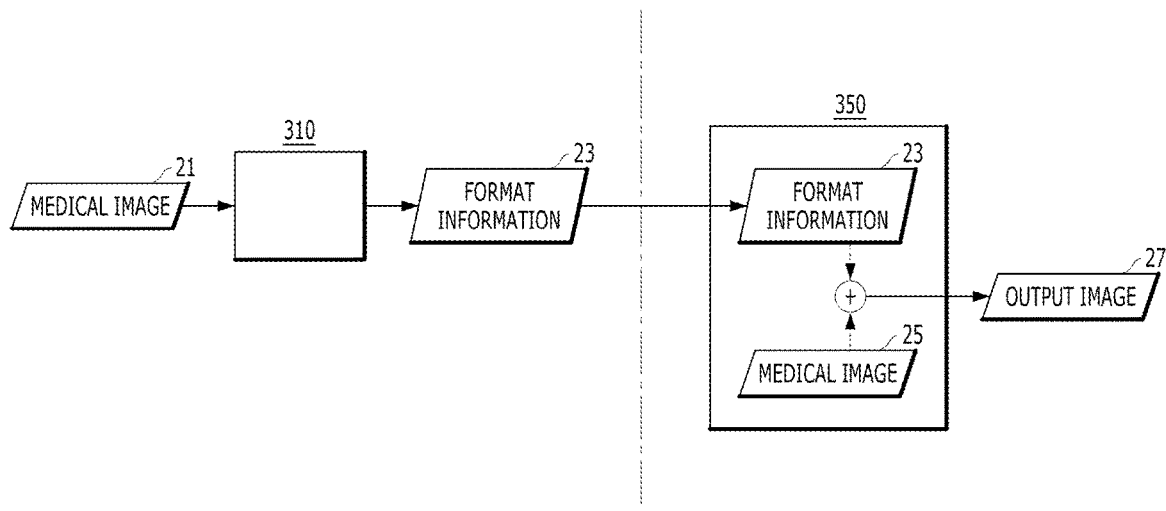

[Figure 3]
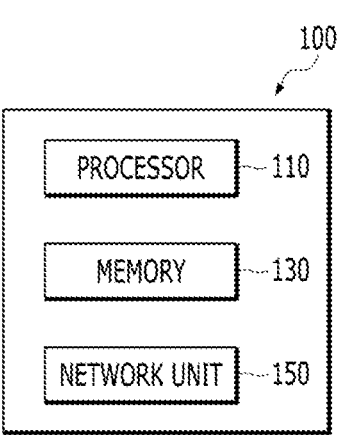

[Figure 4]
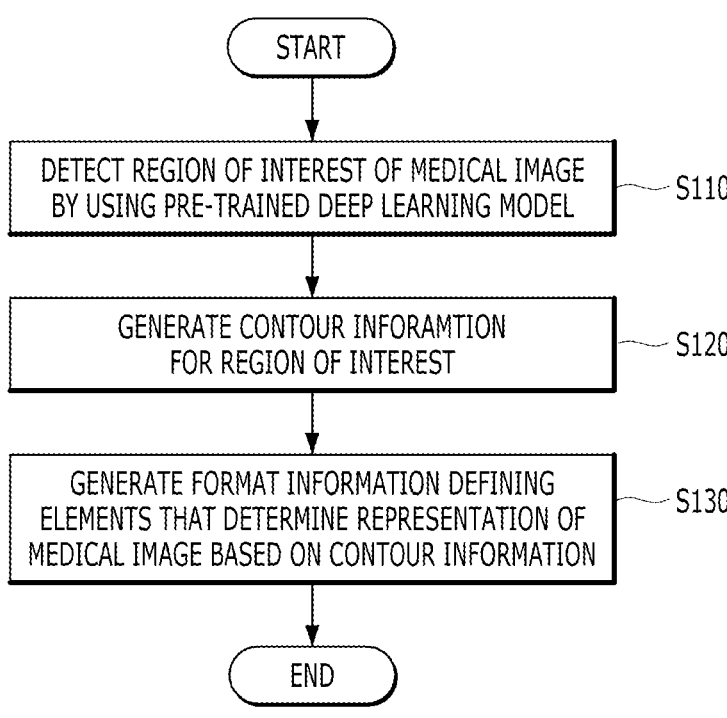
START
DETECT REGION OF INTEREST OF MEDICAL IMAGE
BY USING PRE-TRAINED DEEP LEARNING MODEL     S110
GENERATE CONTOUR INFORAMTION
FOR REGION OF INTEREST     S120
GENERATE FORMAT INFORMATION DEFINING
ELEMENTS THAT DETERMINE REPRESENTATION OF     S130
MEDICAL IMAGE BASED ON CONTOUR INFORMATION
END

[Figure 5]
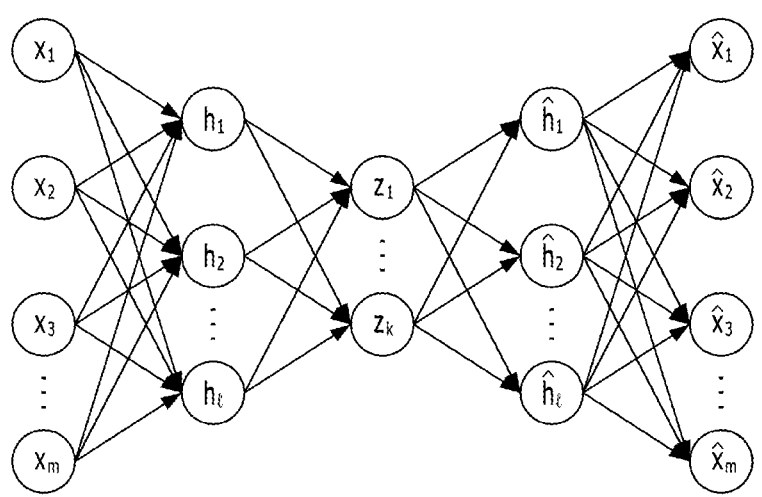

[Figure 6]
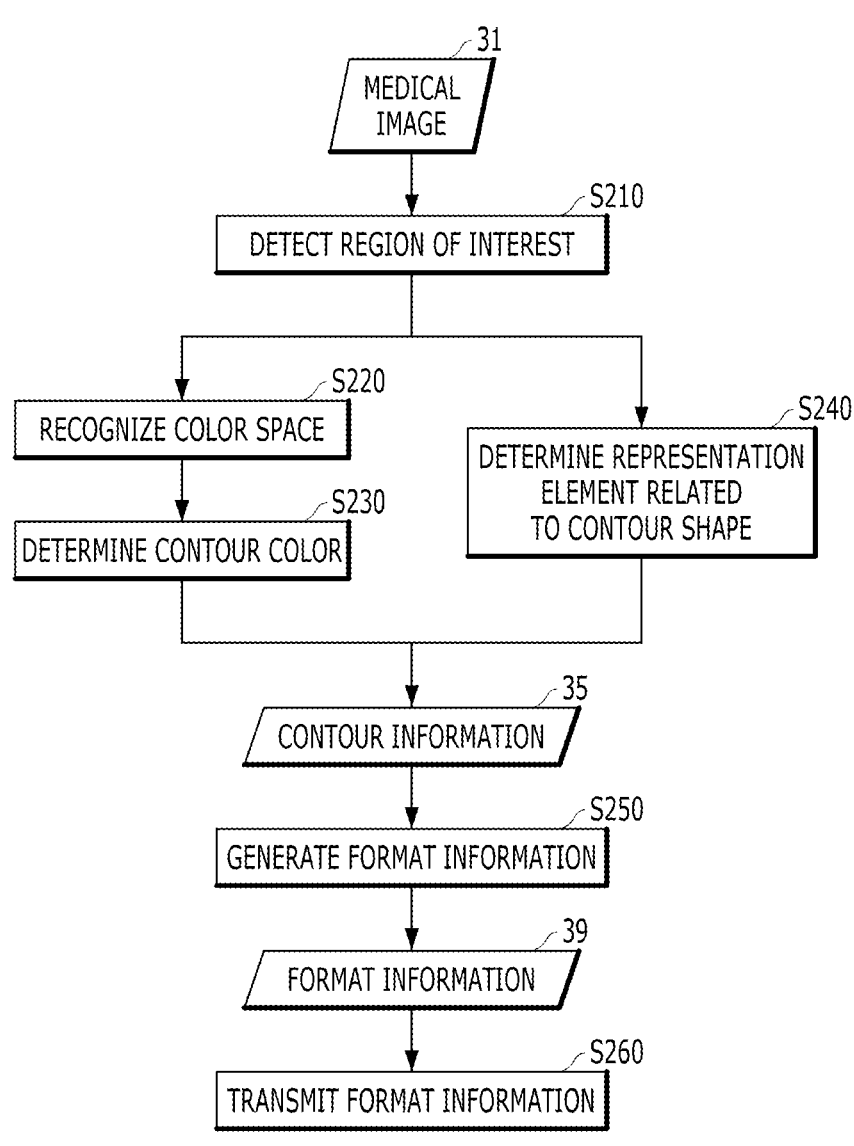

[Figure 7]
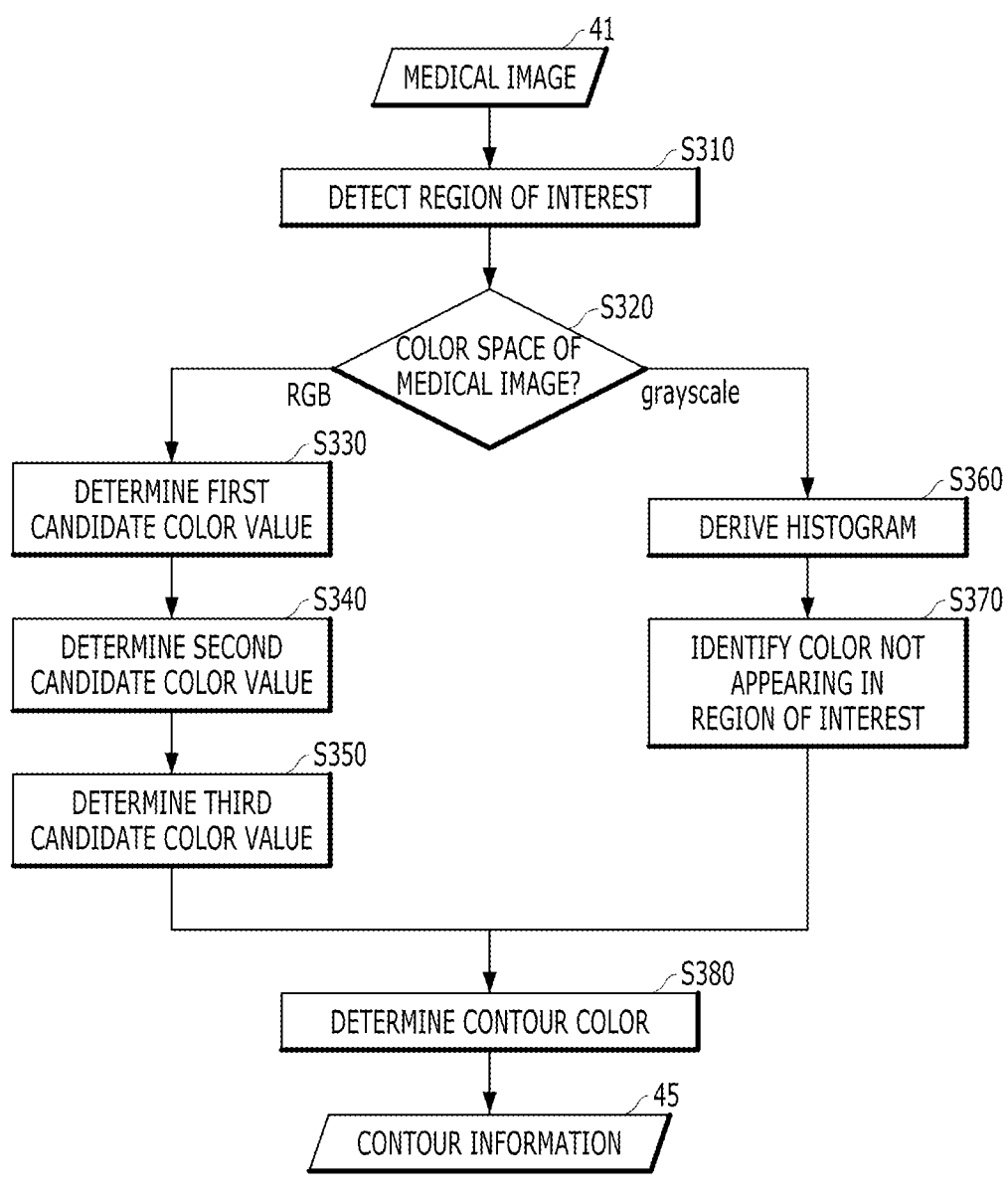

[Figure 8]
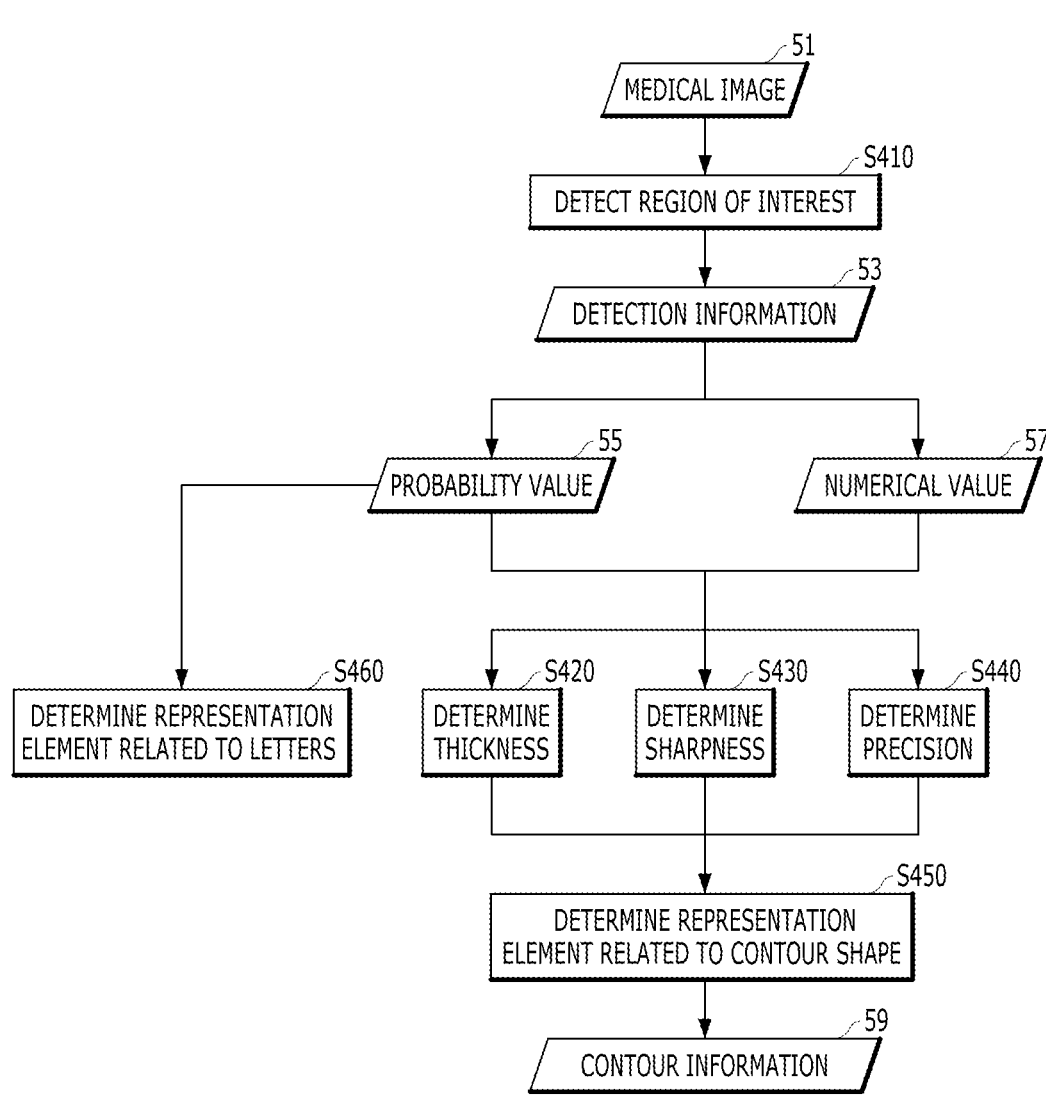

[Figure 9]
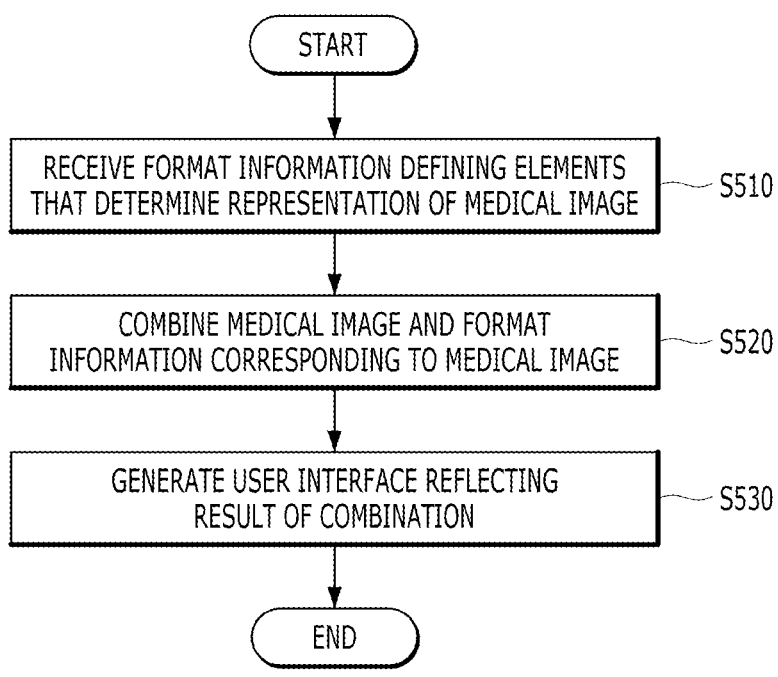

[Figure 10]
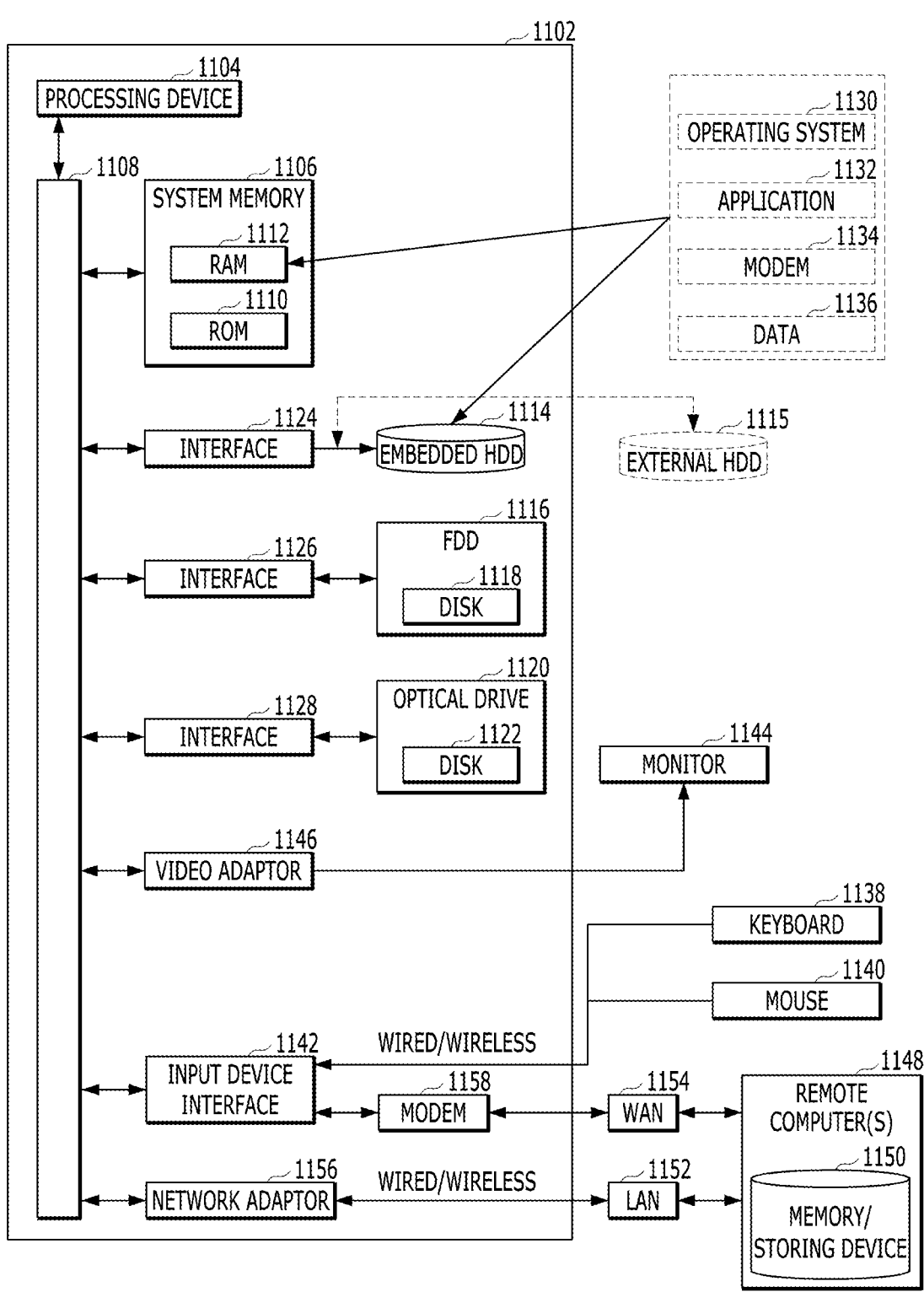

MEDICAL IMAGE PROCESSING METHOD

BACKGROUND

Technical Field

The present disclosure relates to a method of processing a medical image, and more specifically, to a method of analyzing a medical image based on deep learning and effectively providing an analysis result to a user.

Description of the Related Art

Medical images are data that enables people to understand physical states of various organs in the human body. The medical image includes a digital radiographic image (X-ray), a Computed Tomography (CT) image, a Magnetic Resonance Imaging (MRI) image, or the like.

With the development of image analysis technology and artificial intelligence technology, medical images are variously being used as analytical data to aid in the diagnosis of diseases. The current medical system visualizes the analysis results of medical images in various ways and provides system users, such as clinicians, with the visualized analysis results. For example, the current medical system displays the results of analyzing medical images, such as lesion information, on the medical image itself and provides the medical image to the output terminal. In other words, the current medical system transmits the image generated by overlapping the analysis results on the original medical image as they are to the output terminal to provide the analysis results to the user.

In the aforementioned method which is currently used in the medical system, the data corresponding to the analysis result is copied from the original image without change, so that there is the problem in that the data volume is large, and a large number of resources are inevitably required to process the large volume of data. In particular, if the original image is a large-scale image consisting of hundreds of series, the amount of data to process the analysis image on the system is bound to be burdensome. Therefore, it is necessary to develop a technology that can effectively display the analysis results of medical images while reducing the amount of analysis data in the current medical system.

Korean Patent No. 10-1716039 (Mar. 13, 2017) discloses a method and apparatus for calculating disease diagnosis information based on a medical image.

BRIEF DESCRIPTION

Technical Problem

The present disclosure is conceived in response to the foregoing background art, and aims to provide a method of detecting a region of interest of a medical image based on deep learning, and processing data to effectively display a result of the detection.

Technical Solution

A first exemplary embodiment of the present disclosure for implementing the foregoing technical problem provides a medical image processing method performed by a computing device. The medical image processing method includes: detecting a region of interest in a medical image by using a pre-trained deep learning model; determining contour information for the region of interest; and generating, based on the contour information, format information defining elements that determine representation of the medical image.

In an alternative exemplary embodiment, the determining of the contour information for the region of interest may include: identifying a color space of the medical image; and determining a color of a contour marking the region of interest, based on a color distribution of the region of interest in the medical image of which the color space is identified.

In the alternative exemplary embodiment, the determining of the color of the contour marking the region of interest may include determining the color of the contour marking the region of interest based on correlation between colors in the color distribution.

In the alternative exemplary embodiment, when the color space of the medical image is an RGB space, the determining of the color of the contour marking the region of interest may include: deriving a histogram representing a pixel-by-pixel color distribution from the medical image; determining a first candidate color value based on a frequency of occurrence of colors present in the histogram; transforming the color space of the medical image into a Hue Saturation Value (HSV) space, and determining a second candidate color value based on the histogram in the HSV space; determining a third candidate color value in a grayscale based on brightness of pixels included in the medical image; and determining the color of the contour marking the region of interest based on the first candidate color value, the second candidate color value, and the third candidate color value.

In the alternative exemplary embodiment, the determining of the first candidate color value based on the frequency of occurrence of the colors present in the histogram may include determining, based on at least one color having a lowest frequency of occurrence among the colors present in the histogram, at least one color value that prominently represents a predetermined color as the first candidate color value.

In the alternative exemplary embodiment, the determining of the second candidate color value based on the histogram in the HSV space may include: selecting an unoccupied hue from the histogram in the HSV space; selecting saturation and a value of brightness at which visual contrast is prominent based on brightness of pixels included in a candidate region including the region of interest; and determining the second candidate color value based on the selected hue, saturation, and value of brightness.

In the alternative exemplary embodiment, determining of the third candidate color value based on the brightness of the pixels included in the medical image may include: based on the brightness of the pixels included in a candidate region including the region of interest, selecting a color value in a grayscale at which visual contrast is prominent; and determining the selected color value in the grayscale as the third candidate color value.

In the alternative exemplary embodiment, when the color space of the medical image is a grayscale space, the determining of the color of the contour marking the region of interest may include: deriving a histogram representing a pixel-by-pixel color distribution from the medical image; determining at least one color not appearing in the region of interest based on the histogram; and determining, based on the at least one color not appearing in the region of interest, the color of the contour marking the region of interest.

In the alternative exemplary embodiment, the determining of, based on the at least one color not appearing in the region of interest, the color of the contour marking the region of interest may include identifying, based on the at least one color not appearing in the region of interest, colors that are distinguishable from each other in accordance with a type and the number of contours that mark the region of interest.

In the alternative exemplary embodiment, the determining of the contour information for the region of interest may include determining a representation element related to a shape of the contour of the region of interest based on detection information of the region of interest.

In the alternative exemplary embodiment, the detection information may include at least one of a probability value regarding presence of the region of interest or a numerical value of the region of interest, and the representation element related to the shape of the contour of the region of interest includes at least one of a thickness of the contour, sharpness of the contour, precision of the contour, or sharpness of a shadow of the contour.

In the alternative exemplary embodiment, the determining of the representation element related to the shape of the contour of the region of interest based on the detection information of the region of interest may include determining at least one of a thickness of the contour, sharpness of the contour, precision of the contour, or sharpness of a shadow of the contour, based on a magnitude of at least one of a probability value regarding presence of the region of interest or a numerical value of the region of interest. In this case, as the magnitude of at least one of the probability value regarding the presence of the region of interest or the numerical value of the region of interest increases, a magnitude of at least one of the thickness of the contour, the sharpness of the contour, the precision of the contour, or the sharpness of the shadow of the contour may increase.

A second exemplary embodiment of the present disclosure for implementing the foregoing technical problem provides a medical image processing method performed by a computing device. The medical image processing method includes: receiving format information defining elements that determine representation of a medical image; combining the medical image with format information corresponding to the medical image; and generating a user interface reflecting a result of the combination. In this case, the format information may be generated based on contour information for a region of interest of the medical image detected using a pre-trained deep learning model.

Another exemplary embodiment for implementing the foregoing technical problem provides a computer program stored in a computer-readable storage medium. When the computer program is executed in one or more processors, the computer program causes the processor to perform operations for processing a medical image, the operations including: detecting a region of interest in the medical image by using a pre-trained deep learning model; determining contour information for the region of interest; and generating, based on the contour information, format information defining elements that determine a representation layer of the medical image.

Another exemplary embodiment for implementing the foregoing technical problem provides a computing device for processing a medical image. The computing device includes: a processor including at least one core; a memory including program codes executed in the processor; and a network unit for receiving a medical image, in which the processor detects a region of interest in the medical image by using a pre-trained deep learning model, determines contour information for the region of interest, and generates, based on the contour information, format information defining elements that determine a representation layer of the medical image.

Advantageous Effects

The present disclosure may provide a method of detecting a region of interest of a medical image based on deep learning, and processing data to effectively display a result of the detection.

DESCRIPTION OF THE SEVERAL VIEWS OF THE DRAWINGS

FIG. 1 is a block diagram of a system for processing a medical image in the related art.

FIG. 2 is a block diagram of a system for processing a medical image according to an exemplary embodiment of the present disclosure.

FIG. 3 is a block diagram illustrating a computing device for processing a medical image according to the exemplary embodiment of the present disclosure.

FIG. 4 is a flowchart illustrating a medical image processing method according to an exemplary embodiment of the present disclosure.

FIG. 5 is a schematic diagram illustrating a network function according to the exemplary embodiment of the present disclosure.

FIG. 6 is a diagram illustrating a medical image processing process of a computing device according to the exemplary embodiment of the present disclosure.

FIGS. 7 and 8 are diagrams specifically illustrating a process for determining contour information indicative of a region of interest in the computing device according to the exemplary embodiment of the present disclosure.

FIG. 9 is a flowchart illustrating a medical image processing method according to another exemplary embodiment of the present disclosure.

FIG. 10 is a schematic diagram illustrating a computing environment according to an exemplary embodiment of the present disclosure.

DETAILED DESCRIPTION

Various exemplary embodiments will now be described with reference to drawings. In the present specification, various descriptions are presented to provide appreciation of the present disclosure. However, it is apparent that the exemplary embodiments can be executed without the specific description.

"Component," "module," "system," and the like which are terms used in the specification refer to a computer-related entity, hardware, firmware, software, and a combination of the software and the hardware, or execution of the software. For example, the component may be a processing procedure executed on a processor, the processor, an object, an execution thread, a program, and/or a computer, but is not limited thereto. For example, both an application executed in a computing device and the computing device may be the components. One or more components may reside within the processor and/or a thread of execution. One component may be localized in one computer. One component may be distributed between two or more computers. Further, the components may be executed by various computer-readable media having various data structures, which are stored therein. The components may perform communication through local and/or remote processing according to a signal (for example, data transmitted from another system through a network such as the Internet through data and/or a signal from one component that interacts with other components in a local system and a distribution system) having one or more data packets, for example.

The term "or" is intended to mean not exclusive "or" but inclusive "or." That is, when not separately specified or not clear in terms of a context, a sentence "X uses A or B" is intended to mean one of the natural inclusive substitutions. That is, the sentence "X uses A or B" may be applied to any of the case where X uses A, the case where X uses B, or the case where X uses both A and B. Further, it should be understood that the term "and/or" used in this specification designates and includes all available combinations of one or more items among enumerated related items.

It should be appreciated that the term "comprise" and/or "comprising" means presence of corresponding features and/or components. However, it should be appreciated that the term "comprises" and/or "comprising" means that presence or addition of one or more other features, components, and/or a group thereof is not excluded. Further, when not separately specified or it is not clear in terms of the context that a singular form is indicated, it should be construed that the singular form generally means "one or more" in this specification and the claims.

The term "at least one of A or B" should be interpreted to mean "a case including only A," "a case including only B," and "a case in which A and B are combined."

Those skilled in the art need to recognize that various illustrative logical blocks, configurations, modules, circuits, means, logic, and algorithm steps described in connection with the exemplary embodiments disclosed herein may be additionally implemented as electronic hardware, computer software, or combinations of both sides. To clearly illustrate the interchangeability of hardware and software, various illustrative components, blocks, configurations, means, logic, modules, circuits, and steps have been described above generally in terms of their functionalities. Whether the functionalities are implemented as the hardware or software depends on a specific application and design restrictions given to an entire system. Skilled artisans may implement the described functionalities in various ways for each particular application. However, such implementation decisions should not be interpreted as causing a departure from the scope of the present disclosure.

The description of the presented exemplary embodiments is provided so that those skilled in the art of the present disclosure use or implement the present disclosure. Various modifications to the exemplary embodiments will be apparent to those skilled in the art. Generic principles defined herein may be applied to other embodiments without departing from the scope of the present disclosure. Therefore, the present disclosure is not limited to the exemplary embodiments presented herein. The present disclosure should be analyzed within the widest range which is coherent with the principles and new features presented herein.

In the present disclosure, a network function and an artificial neural network and a neural network may be interchangeably used.

In the meantime, the term "image" or "video" used throughout the detailed description and the claims of the present disclosure refer to multidimensional data composed of discrete image elements (for example, pixels in a 2-dimensional image), and in other words, is the term referring to a target visible to the eye (for example, displayed on a video screen) or a digital representation of the target (for example, a file corresponding to a pixel output of a CT or MRI detector).

For example, "image" or "video" may be a medical image of a subject collected by Computed Tomography (CT), Magnetic Resonance Imaging (MRI), fundus image, ultrasonic rays, or other predetermined medical imaging systems publicly known in the art of the present disclosure. The image is not necessarily provided in a medical context, but may also be provided in a non-medical context, such as X-ray imaging for security screening.

Throughout the detailed description and the claims of the present disclosure, the "Digital Imaging and Communications in Medicine (DICOM)" standard is a term collectively referring to various standards used in digital imaging expression and communication in medical devices, and the DICOM standard is published by the allied committee formed by the American College of Radiology (ACR) and American National Electrical Manufacturers Associations (NEMA).

Also, throughout the detailed description and claims of the present disclosure, the term "Picture Archiving and Communication System (PACS)" refers to a system that stores, processes, and transmits medical images in accordance with the DICOM standard. In a Picture Archiving and Communication System (PACS), medical images acquired by using digital medical imaging equipment, such as X-rays, CTs, and MRIs, are stored in DICOM format and may be transmitted to terminals inside and outside the hospital through a network, to which reading results and medical records may be added.

FIG. 1 is a block diagram of a system for processing a medical image in the related art.

Referring to FIG. 1, a system in the related art includes a first computing device 210 for receiving a medical image 11 as input, performing an analysis, generating an analysis image 15 based on the analysis result, and a second computing device 250 for generating an output image 17 displaying the analysis result based on the analysis image 15. When the analysis of the medical image 11 is completed, the first computing device 210 overlays analysis information 13 generated as the result of the analysis on the medical image 11 to generate the analysis image 15. The second computing device 250 receives the analysis image 15 from the first computing device 210 and generates an output image 17. In this case, the output image 17 may be the analysis image 15 itself, or may also be an image generated by further processing of the analysis image 15.

The analysis image 15 generated by the first computing device 210 of the system in the related art is an image in which the analysis information 13 overlaps the medical image 11 itself that is the original image. That is, the analysis image 15 includes the analysis information 13 along with the medical image 11 itself (or a copy of the medical image 11) that is the original image. Therefore, the analysis image 15 inevitably has a larger capacity than the medical image 11. Furthermore, the large capacity of the analysis image 15 inevitably places a burden on the processing operations, such as data transception between the computing devices 210 and 250, and image generation or the analysis result output by the computing devices 210 and 250.

For example, in the system in the related art, the first computing device 210 is a server that analyzes lesions in the medical image, and the second computing device 250 is a PACS viewer terminal. The lesion analysis server, which is the first computing device 210, receives the medical image, analyzes a lesion area, and overlays the medical image with information about the lesion area to generate a Secondary Capture (SC) image. In this case, the SC image is data in a DICOM format for output on the PACS viewer terminal, which is the second computing device 250. Since the SC image (that is, SC DICOM data) is a copy of the original medical image as it is, the SC image inevitably has a fairly large capacity. In particular, when the medical image is a three-dimensional image, the original image is 100 to 200 DICOM-format series data, so the SC image in the DICOM format is inevitably generated in a large capacity of tens to hundreds of megabytes (MB), which is burdensome for computing resources to process. In other words, sharing DICOM-format SC images between devices and outputting lesion analysis results based on DICOM-format SC images through the system in the related art places a significant burden on computing resources for image processing and makes it difficult to provide efficient and effective analysis results.

FIG. 2 is a block diagram of a system for processing a medical image according to an exemplary embodiment of the present disclosure.

Referring to FIG. 2, a system according to an exemplary embodiment of the present disclosure may include a first computing device 310 for receiving a medical image 21 as input, performing an analysis, and generating format information 23 defining elements that determine the representation of the medical image based on a result of the analysis, and a second computing device 350 for receiving the format information 23 as input and generating an output image 27 displaying the result of the analysis of the medical image. Rather than overlaying the medical image 21 with the result of the analysis, the first computing device 310 may generate the analysis result for the medical image 21 as separate format information 23 that may be combined with the medical image 21. The first computing device 310 may generate the format information 23 about the elements that determine the representation of the result of the analysis for the medical image 21 in the medical image 21 and transmit the generated format information 23 to the second computing device 350. The second computing device 350 may receive the format information 23 and combine the format information 23 with the medical image 25 to generate the output image 27 for displaying the result of the analysis. In this case, the medical image 25 may be an image corresponding to the format information 23 pre-stored in the second computing device 350, or may be the medical image 21 corresponding to the original transmitted from the first computing device 310.

The format information 23 generated by the first computing device 310 of the present disclosure may include main information for displaying the result of the analysis of the medical image 21 on the image, excluding the medical image that is the original image. In other words, the format information 23 may be understood not as image data, but as data that defines elements that determine the representation of the medical image for the analysis result, such as the type of medical image to which the analysis result is matched, and the region of the image in which the analysis result is to be displayed. Thus, the format information 23 may be generated in a smaller capacity than the analysis image 15 of the system in the related art illustrated in FIG. 1, without including the image itself and without losing important analysis result. A small capacity of the format information 23 may reduce the burden on the processing operations, such as data transception between computing devices 310 and 350, image generation or analysis result output by the computing devices 310 and 350.

The output image 27 generated by the second computing device 350 of the present disclosure may be understood as data generated through the combination of the format information 23 and the medical image 25. The format information 23 defines various specifications that determine what information is to be represented in which medical image. Thus, by coupling the format information 23 to the medical image 25, the second computing device 350 may easily generate the output image 27 that accurately represents the result of the analysis by the first computing device 310. In this way, when the output image 27 is generated by utilizing the format information 23, it is possible to reduce the resources required for data processing to display the result of the analysis. Furthermore, since the format information 23 defines various representation elements of the analysis result, when the output image 27 is generated by utilizing the format information 23, the visual display effect for the analysis result may be greatly improved compared to the system in the related art.

For example, the first computing device 310 may be a server that analyzes lesions in medical images, and the second computing device 350 may be one of terminals included in a PACS, according to the exemplary embodiment of the present disclosure. The lesion analysis server that is the first computing device 310 may receive a medical image as input and analyze lesion regions by using a pre-trained deep learning model. Then, the lesion analysis server that is the first computing device 310 may generate Grayscale Softcopy Presentation State (GSPS) information, which is one of the format information that defines the image representation elements for the lesion region. In this case, the GSPS information is a DICOM object that defines the elements determining the display state of a DICOM image, and may include information related to displaying the state of the image on the screen. In other words, GSPS information represents the data elements that define in which image file lesion analysis information is to be displayed and where lesion analysis information is to be displayed. Thus, even when a medical image is a three-dimensional image consisting of 100 to 200 DICOM-format series data, the GSPS information is not the image data itself and thus may be generated in a small capacity of a few kilobytes (KB) to a few megabytes (MB), which is easier for computing resources to process. The PACS terminal that is the second computing device 350 may match the GSPS information to the DICOM-formatted image to generate an image or a user interface for providing information about the lesion area.

The system according to the exemplary embodiment of the present disclosure is capable of discriminating and processing the image data in the DICOM format and the GSPS data defining representation elements for lesion regions, which may significantly reduce the data processing burden on the computing resources. Furthermore, according to the exemplary embodiment of the present disclosure, the GSPS file enables standardization of a screen display state of an image, so that quality-assured analysis results may be provided to a system user without affecting the computing resource environment, such as an image capturing device and an output device. In other words, the utilization of the GSPS files in the system according to the exemplary embodiment of the present disclosure may provide an environment for efficient and effective data visualization processing and provision of analysis results.

The specific descriptions of the types of format information, such as GSPS, are just examples based on the assumed computing environment of the medical system. Accordingly, the types of format information are not limited to the foregoing examples (that is, GSPS), but may vary within the understandable range by those skilled in the art depending on the computing environment of the medical system.

FIG. 3 is a block diagram illustrating the computing device for processing a medical image according to the exemplary embodiment of the present disclosure.

A configuration of the computing device 100 illustrated in FIG. 3 is only an example shown through simplification. In an exemplary embodiment of the present disclosure, the computing device 100 may include other components for performing a computing environment of the computing device 100 and only some of the disclosed components may constitute the computing device 100.

The computing device 100 may include a processor 110, a memory 130, and a network unit 150.

The processor 110 may be constituted by one or more cores and may include processors for data analysis and deep learning, which include a central processing unit (CPU), a general purpose graphics processing unit (GPGPU), a tensor processing unit (TPU), and the like of the computing device. The processor 110 may read a computer program stored in the memory 130 to perform data processing for machine learning according to an exemplary embodiment of the present disclosure. According to an exemplary embodiment of the present disclosure, the processor 110 may perform a calculation for learning the neural network. The processor 110 may perform calculations for learning the neural network, which include processing of input data for learning in deep learning (DL), extracting a feature in the input data, calculating an error, updating a weight of the neural network using backpropagation, and the like. At least one of the CPU, GPGPU, and TPU of the processor 110 may process learning of a network function. For example, both the CPU and the GPGPU may process the learning of the network function and data classification using the network function. Further, in an exemplary embodiment of the present disclosure, processors of a plurality of computing devices may be used together to process the learning of the network function and the data classification using the network function. Further, the computer program executed in the computing device according to an exemplary embodiment of the present disclosure may be a CPU, GPGPU, or TPU executable program.

According to the exemplary embodiment of the present disclosure, the processor 110 may detect regions of interest in the medical image by using a pre-trained deep learning model. For example, the processor 110 may perform a task for detecting a lesion, such as detection, segmentation, or classification of a region of interest in a medical image, by using a pre-trained deep learning model. The processor 110 may detect regions in a medical image that are determined to be lesions by performing tasks, such as detection, segmentation, or classification, by using the deep learning model. In this case, the medical image may include both two-dimensional and three-dimensional images. In addition, the medical image may include not only single image, but also series of images and multiple images in a time series relationship.

The processor 110 may determine contour information of the region of interest detected by the deep learning model. The processor 110 may generate contour information for the region of interest based on the detection information of the region of interest derived by the deep learning model to distinguish and display the region of interest from the rest of the medical region. In this case, the contour information may include color info-nation, shape information, and the like of the contour representing the region of interest. For example, the processor 110 may generate color information by determining a color of the contour based on the detection information of the region of interest and the color space configuring the medical image. In this case, the color of the contour may be determined by considering the color of the surrounding region of the region of interest, the type of region of interest, the number of regions of interest, and the like. Further, the processor 110 may generate shape information by determining representation elements associated with the shape of the contour based on the detection information of the region of interest. In this case, the representation element related to the shape of the contour may be determined by considering the type of region of interest and the number of regions of interest.

Based on the contour information, the processor 110 may generate format information that defines the elements determining the representation of the medical image. The format information defines the representation elements for visualizing the region of interest based on the information related to the region of interest. The processor 110 may discriminate visualization information including the contour information of the region of interest from the medical image to generate the visualization information as format information that is separate data. The format information generated by the processor 110 may ensure the quality of visualization of the detection information while having a capacity advantage over the existing method of displaying all the information in the image. For example, when the medical image is a DICOM image, the processor 110 may generate GSPS information that defines elements determining the representation layer of the DICOM image based on the aforementioned result of the analysis of the region of interest. In this case, the GSPS information may include information about the DICOM image to be matched (or referenced), detection information and contour information of the region of interest to be visually represented in the DICOM image to be matched, and the like.

In an alternative exemplary embodiment, when the computing device 100 is a device for outputting or providing a user with a result of an analysis of a medical image, the processor 110 may combine the medical image with format information corresponding to the medical image. When the result of the analysis of the region of interest in the medical image need to be provided to a user, the processor 110 may combine the format information and the medical image to generate an image that represents the result of the analysis of the region of interest. For example, when the medical image is a DICOM image, the processor 110 may combine the GSPS information with the DICOM image to generate an image that displays information about lesions detected through the analysis using a deep learning model. Since the GSPS information defines which regions of what kind of DICOM image to represent the lesion in, the processor 110 may refer to the GSPS information to generate a medical image that visually represents the lesion from the medical image corresponding to the GSPS information.

The processor 110 may generate a user interface based on the image generated by the combination of the medical image and the format information. The processor 110 may generate a user interface based on the medical image, which represents all of detection information, contour information, and the like of the region of interest included in the format information. For example, the processor 110 may generate a user interface to assist in the diagnosis of a disease based on a DICOM image showing expected lesions on a body part generated by combining the DICOM image with GSPS information. In this case, the DICOM image output through the user interface may display the contour of the region predicted to be the lesion represented based on the GSPS information, as well as the detection information of the lesion (for example, probability of presence, size, and volume). In this case, the contour of the region predicted to be a lesion may be expressed on the DICOM image to distinguish colors, shapes, and the like based on the GSPS information, in consideration of the type and the number of lesions.

According to an exemplary embodiment of the present disclosure, the memory 130 may store any type of information generated or determined by the processor 110 and any type of information received by the network unit 150.

According to an exemplary embodiment of the present disclosure, the memory 130 may include at least one type of storage medium of a flash memory type storage medium, a hard disk type storage medium, a multimedia card micro type storage medium, a card type memory (for example, an SD or XD memory, or the like), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk. The computing device 100 may operate in connection with a web storage performing a storing function of the memory 130 on the Internet. The description of the memory is just an example and the present disclosure is not limited thereto.

The network unit 150 according to an exemplary embodiment of the present disclosure may use an arbitrary type known wired/wireless communication systems.

The network unit 150 may receive a medical image depicting at least a portion of a body from a medical imaging device (or system). For example, a medical image depicting at least a portion of a body may be data for training or data for inference for a deep learning model trained with two-dimensional or three-dimensional features. The medical image depicting at least a portion of a body may include all of the images, such as a three-dimensional T1 MR image, X-ray images, CT images, and pathology slide images, related to the organ of the body obtained through the photographing.

In an alternative exemplary embodiment, the network unit 150 may also receive analysis data of the medical image from a device (or system) for analyzing medical images. In this case, the analysis data of the medical image may include data in a specific format that defines elements for visually representing the result of the analysis of the medical image. For example, the analysis data from a medical image may be GSPS data including contour information of lesions detected by the deep learning model. However, as this is only one example, the analysis data of the medical image is not limited to the example of the GSPS and may be varied within the scope understood by those skilled in the art.

On the other hand, the network unit 150 may transmit and receive information processed by the processor 110, a user interface, and the like with other terminals through communication. For example, the network unit 150 may provide the user interface generated by the processor 110 to a client (for example, a user terminal). Further, the network unit 150 may receive the external input of the user applied to the client and transmit the received external input to the processor 110. In this case, the processor 110 may process the operations of output, correction, change, addition, and the like of the information provided through the user interface based on the external input of the user received from the network unit 150.

Although not illustrated in FIG. 3, the computing device 100 may also include an input unit and an output unit.

The input unit according to an alternative exemplary embodiment of the present disclosure may include keys and/or buttons on a user interface or physical keys and/or buttons for receiving user input. According to the user input through the input unit, a computer program may be executed to control the display according to the exemplary embodiments of the present disclosure.

The input unit may receive signals by detecting button press or touch input from the user, or may receive voice or motion from the user through a camera or microphone and convert the received voice or motion into an input signal. To this end, speech recognition technology or motion recognition technology may be used.

The input unit may also be implemented as external input equipment connected to the computing device 100. For example, the input equipment may be at least one of a touch pad, a touch pen, a keyboard, and a mouse for receiving a user input, but this is merely an example, and the present disclosure is not limited thereto.

The input unit may recognize user touch input. The input unit according to the exemplary embodiment of the present disclosure may have the same configuration as the output unit. The input unit may include a touch screen implemented to receive a user's selection input. In the touch screen, any one of a contact type capacitance method, an infrared light sensing method, a Surface Ultrasonic Wave (SAW) method, a piezoelectric method, and a resistive film method may be used. The detailed description for the foregoing touch screen is merely illustrative according to the exemplary embodiments of the present disclosure, and various touch screen panels may be applied to the computing device 100. The input unit configured as a touch screen may include a touch sensor. A touch sensor may be configured to convert changes in pressure applied to a particular part of the input unit or capacitance generated in a particular part of the input unit into an electrical input signal. The touch sensor may be configured to detect not only the touched position and area, but also the pressure at the time of touch. When a touch input is made to the touch sensor, a signal(s) corresponding to the touch input is transmitted to a touch controller. The touch controller processes the signal(s) and then transmits data corresponding to the signal(s) to the processor 110. This allows the processor 110 to recognize, for example, which areas of the input unit have been touched.

The output unit according to an alternative exemplary embodiment of the present disclosure may output any form of information generated or determined by the processor 110, or any form of information received by the user interface and the network unit 150.

For example, the output unit may include at least one of a Liquid Crystal Display (LCD), a Thin Film Transistor Liquid Crystal Display (TFT LCD), an Organic Light Emitting Diode (OLED), a flexible display, and a 3D display. Among them, some display modules may be configured as a transparent type or a light transmission type so that the outside can be seen through the display modules. This may be referred to as a transparent display module, and a representative example of the transparent display module includes a Transparent OLED (TOLED).

In the meantime, the computing device 100 according to the exemplary embodiment of the present disclosure is a computing system for transceiving information with the client through communication and may include a server. In this case, the client may be a predetermined type of terminal accessible to the server. For example, the computing device

100, which is a server, may receive medical images from a medical imaging terminal, detect lesions, and provide a user interface including a result of the detection to the user terminal. In this case, the user terminal may output the user interface received from the computing device 100 that is the server, and receive or process information through interaction with the user.

In an additional exemplary embodiment, the computing device 100 may also include a predetermined form of a terminal which receives data resources generated in a predetermined server and performs additional information processing.

FIG. 4 is a flowchart illustrating a medical image processing method according to an exemplary embodiment of the present disclosure. Further, FIG. 5 is a schematic diagram illustrating a network function according to the exemplary embodiment of the present disclosure.

Referring to FIG. 4, in operation S100, the computing device 100 according to the exemplary embodiment of the present disclosure may detect a region of interest in a medical image by using a pre-trained deep learning model. In this case, referring to FIG. 5, the deep learning model according to the exemplary embodiment of the present disclosure may include a neural network capable of detecting, segmenting, or classifying a region of interest included in the medical image. Throughout the present specification, the neural network, a network function, and the neural network may be used as the same meaning. The neural network may be generally constituted by an aggregate of calculation units which are mutually connected to each other, which may be called nodes. The nodes may also be called neurons. The neural network is configured to include one or more nodes. The nodes (alternatively, neurons) constituting the neural networks may be connected to each other by one or more links. In the neural network, one or more nodes connected through the link may relatively form the relationship between an input node and an output node. Concepts of the input node and the output node are relative and a predetermined node which has the output node relationship with respect to one node may have the input node relationship in the relationship with another node and vice versa. As described above, the relationship of the input node to the output node may be generated based on the link. One or more output nodes may be connected to one input node through the link and vice versa.

In the relationship of the input node and the output node connected through one link, a value of data of the output node may be determined based on data input in the input node. Here, a link connecting the input node and the output node to each other may have a weight. The weight may be variable and the weight is variable by a user or an algorithm in order for the neural network to perform a desired function. For example, when one or more input nodes are mutually connected to one output node by the respective links, the output node may determine an output node value based on values input in the input nodes connected with the output node and the weights set in the links corresponding to the respective input nodes.

As described above, in the neural network, one or more nodes are connected to each other through one or more links to form a relationship of the input node and output node in the neural network. A characteristic of the neural network may be determined according to the number of nodes, the number of links, correlations between the nodes and the links, and values of the weights granted to the respective links in the neural network. For example, when the same number of nodes and links exist and there are two neural networks in which the weight values of the links are different from each other, it may be recognized that two neural networks are different from each other.

The neural network may be constituted by a set of one or more nodes. A subset of the nodes constituting the neural network may constitute a layer. Some of the nodes constituting the neural network may constitute one layer based on the distances from the initial input node. For example, a set of nodes of which distance from the initial input node is n may constitute n layers. The distance from the initial input node may be defined by the minimum number of links which should be passed through for reaching the corresponding node from the initial input node. However, a definition of the layer is predetermined for description and the order of the layer in the neural network may be defined by a method different from the aforementioned method. For example, the layers of the nodes may be defined by the distance from a final output node.

The initial input node may mean one or more nodes in which data is directly input without passing through the links in the relationships with other nodes among the nodes in the neural network. Alternatively, in the neural network, in the relationship between the nodes based on the link, the initial input node may mean nodes which do not have other input nodes connected through the links. Similarly thereto, the final output node may mean one or more nodes which do not have the output node in the relationship with other nodes among the nodes in the neural network. Further, a hidden node may mean nodes constituting the neural network other than the initial input node and the final output node.

In the neural network according to an exemplary embodiment of the present disclosure, the number of nodes of the input layer may be the same as the number of nodes of the output layer, and the neural network may be a neural network of a type in which the number of nodes decreases and then, increases again from the input layer to the hidden layer. Further, in the neural network according to another exemplary embodiment of the present disclosure, the number of nodes of the input layer may be smaller than the number of nodes of the output layer, and the neural network may be a neural network of a type in which the number of nodes decreases from the input layer to the hidden layer. Further, in the neural network according to yet another exemplary embodiment of the present disclosure, the number of nodes of the input layer may be larger than the number of nodes of the output layer, and the neural network may be a neural network of a type in which the number of nodes increases from the input layer to the hidden layer. The neural network according to still yet another exemplary embodiment of the present disclosure may be a neural network of a type in which the neural networks are combined.

A deep neural network (DNN) may refer to a neural network that includes a plurality of hidden layers in addition to the input and output layers. When the deep neural network is used, the latent structures of data may be determined. That is, latent structures of photos, text, video, voice, and music (e.g., what objects are in the photo, what the content and feelings of the text are, what the content and feelings of the voice are) may be determined. The deep neural network may include a convolutional neural network (CNN), a recurrent neural network (RNN), an auto encoder, generative adversarial networks (GAN), a restricted Boltzmann machine (RBM), a deep belief network (DBN), a Q network, a U network, a Siam network, a Generative Adversarial Network (GAN), and the like. The description of the deep neural network described above is just an example and the present disclosure is not limited thereto.

In an exemplary embodiment of the present disclosure, the network function may include the auto encoder. The auto encoder may be a kind of artificial neural network for outputting output data similar to input data. The auto encoder may include at least one hidden layer and odd hidden layers may be disposed between the input and output layers. The number of nodes in each layer may be reduced from the number of nodes in the input layer to an intermediate layer called a bottleneck layer (encoding), and then expanded symmetrical to reduction to the output layer (symmetrical to the input layer) in the bottleneck layer. The auto encoder may perform non-linear dimensional reduction. The number of input and output layers may correspond to a dimension after preprocessing the input data. The auto encoder structure may have a structure in which the number of nodes in the hidden layer included in the encoder decreases as a distance from the input layer increases. When the number of nodes in the bottleneck layer (a layer having a smallest number of nodes positioned between an encoder and a decoder) is too small, a sufficient amount of information may not be delivered, and as a result, the number of nodes in the bottleneck layer may be maintained to be a specific number or more (e.g., half of the input layers or more).

The neural network may be learned in at least one scheme of supervised learning, unsupervised learning, semi supervised learning, or reinforcement learning. The learning of the neural network may be a process in which the neural network applies knowledge for performing a specific operation to the neural network.

The neural network may be learned in a direction to minimize errors of an output. The learning of the neural network is a process of repeatedly inputting training data into the neural network and calculating the output of the neural network for the training data and the error of a target and back-propagating the errors of the neural network from the output layer of the neural network toward the input layer in a direction to reduce the errors to update the weight of each node of the neural network. In the case of the supervised learning, the training data labeled with a correct answer is used for each training data (i.e., the labeled training data) and in the case of the unsupervised learning, the correct answer may not be labeled in each training data. That is, for example, the training data in the case of the supervised learning related to the data classification may be data in which category is labeled in each training data. The labeled training data is input to the neural network, and the error may be calculated by comparing the output (category) of the neural network with the label of the training data. As another example, in the case of the unsupervised learning related to the data classification, the training data as the input is compared with the output of the neural network to calculate the error. The calculated error is back-propagated in a reverse direction (i.e., a direction from the output layer toward the input layer) in the neural network and connection weights of respective nodes of each layer of the neural network may be updated according to the back propagation. A variation amount of the updated connection weight of each node may be determined according to a learning rate. Calculation of the neural network for the input data and the back-propagation of the error may constitute a learning cycle (epoch). The learning rate may be applied differently according to the number of repetition times of the learning cycle of the neural network. For example, in an initial stage of the learning of the neural network, the neural network ensures a certain level of performance quickly by using a high learning rate, thereby increasing efficiency and uses a low learning rate in a latter stage of the learning, thereby increasing accuracy.

In learning of the neural network, the training data may be generally a subset of actual data (i.e., data to be processed using the learned neural network), and as a result, there may be a learning cycle in which errors for the training data decrease, but the errors for the actual data increase. Overfitting is a phenomenon in which the errors for the actual data increase due to excessive learning of the training data. For example, a phenomenon in which the neural network that learns a cat by showing a yellow cat sees a cat other than the yellow cat and does not recognize the corresponding cat as the cat may be a kind of overfitting. The overfitting may act as a cause which increases the error of the machine learning algorithm. Various optimization methods may be used in order to prevent the overfitting. In order to prevent the overfitting, a method such as increasing the training data, regularization, dropout of omitting a part of the node of the network in the process of learning, utilization of a batch normalization layer, etc., may be applied.

Referring to FIG. 4, in operation S200, the computing device 100 according to the exemplary embodiment of the present disclosure may determine contour information for the detected region of interest in the medical image through the deep learning model described above. The contour information is information for visually representing one region of the medical image corresponding to the region of interest, and may include information about the color and shape of the contour. The computing device 100 may generate the contour information by determining representation elements related to the color of the contour and the shape of the contour based on the detection information for the region of interest and the information about the representation elements in the medical image.

Specifically, the computing device 100 may determine the color of the contour marking the region of interest based on color distribution of the region of interest in the medical image. It can be understood that the color determination of the contour is performed to clearly distinguish the region of interest from the surrounding region through color, so that the region of interest is well represented visually. For example, the computing device 100 may identify a color space of the medical image. The computing device 100 may recognize the color distribution of the region of interest in the medical image for which the color space is identified. The computing device 100 may then determine the color of the contour marking the region of interest based on the correlation between the colors in the color distribution. In other words, the computing device 100 may recognize the distribution of colors in the color space of the medical image, and then determine the color of the contour that may highlight the region of interest based on the colors that contrast with the colors used in the region of interest, or the colors in a complementary relationship with the colors used in the region of interest. In this case, the computing device 100 may determine the color of the contour by performing operation while distinguishing a separate pipeline for determining the color based on the color space of the medical image. That is, the computing device 100 may perform different computations to determine the color of the contour depending on whether the color space of the medical image is an RGB space or a grayscale space. This will be described in more detail later with reference to FIGS. 7 and 8.

Further, the computing device 100 may determine representation elements associated with the shape of the contour of the region of interest based on the detection information of the region of interest. The computing device 100 may reflect numerical changes in the detection information of the region of interest in changes in the shape of the contour to determine what values the representation elements associated with the shape of the contour need to have. In other words, the determination of the shape of the contour may be understood to be performed to allow the user to intuitively understand the analysis result of the region of interest through a visual representation of the region of interest associated with the prediction result of the deep learning model. For example, the detection information of the region of interest is information about the region of interest predicted by the deep learning model, which may include a predicted probability value of the region of interest, numerical values indicating the size, volume, and the like of the region of interest, and the like. The representation elements related to the shape of the contour are elements that define how the contour will appear externally, and may include the shape, thickness, sharpness, and precision of the contour, and sharpness of the contour shadow. An increase in the predicted probability value for the region of interest means that a probability that the region predicted by the deep learning model corresponds to the region of interest is increased. Accordingly, the computing device 100 may determine the representation element associated with the shape of the contour such that the thickness of the contour increases as the predicted probability value of the region of interest increases, in order to indicate how accurately the deep learning model predicted the region of interest.

In operation S300, the computing device 100 may generate format information defining elements that determine the representation of the medical image based on the contour information of the region of interest. The format information may define, as data separate from the medical image, which part of the medical image the result of the detection of the region of interest contained in the medical image to be shown and what needs to be shown. In other words, the format information is not generated by displaying detection results on the image itself, but is data that defines representation elements independently of the image. Therefore, generating and utilizing the format information may reduce the capacity burden of data processing for visualizing the analysis result of the medical image, and ensure the quality of visualization that may achieve stable representation regardless of the image capturing environment or type of image. For example, when the medical image is a DICOM image, the computing device 100 may generate GSPS information that defines, for example, the contour color and shape of the region of interest. The GSPS information may be generated regardless of the type of imaging equipment used to acquire the DICOM image and may be generated as data independent of the original DICOM image that is a target of the analysis. The GSPS information, which defines the representation elements for the color and shape of the contour, may be utilized not only when the color space of a medical image is a grayscale space, but also when the color space of the medical image is an RBG space, such as pathology images. GSPS information may be used more effectively in a pathology image, where the color of the region of interest may vary depending on the color of the slide being stained.

FIG. 6 is a diagram illustrating a medical image processing process of the computing device according to the exemplary embodiment of the present disclosure.

Referring to FIG. 6, the computing device 100 according to the exemplary embodiment of the present disclosure may detect a region of interest to assist diagnosis based on a medical image 31 by using a pre-trained deep learning model (S210). The computing device 100 may generate contour information 35 that determines a visual representation element of the region of interest based on a result of the detection of the region of interest. Specifically, the computing device 100 may identify a color space of the medical image 31 (S220). In this context, the color space refers to a specific space that represents the color signal of an image, which may be differentiated into a grayscale space, an RGB space, a Hue Saturation Value (HSV) space, etc., depending on the type of color signal. The computing device 100 may recognize a color distribution of the medical image 31 for which the color space is identified to determine a contour color so that the region of interest stands out from surrounding areas (S230). Further, the computing device 100 may determine a representation element associated with a contour shape of the region of interest by reflecting the result of the detection of the region of interest in the contour shape of the region of interest to enable intuitive determination of a user about the result of the detection of the region of interest (S250). In other words, the computing device 100 may determine a numerical indicator of each element such that the thickness, sharpness, precision, and the like of the contour, which are representation elements related to the contour shape, are represented according to the result of the detection of the region of interest. When the contour information 35 is determined through the process described above, the computing device 100 may generate format information 39 including the contour information 35 (S250). Herein, the format information 39 may be understood as information that defines elements, such as location, contour color, and contour shape, of the region of interest to be represented in the medical image. The generation of the format information 39 may dramatically reduce the capacity of data required to show the result of the analysis of the medical image 31. The computing device 100 may transmit the format information 39 to a terminal that outputs the result of the analysis of the medical image 31 (S260). Because the format information 39 itself has low capacity, the computing device 100 may handle the data transmission more efficiently than transmitting the analysis image itself in the existing method.

FIG. 7 is a diagram specifically illustrating a process for determining contour color of a region of interest included in a medical image in the computing device according to the exemplary embodiment of the present disclosure.

Operation S310 shown in FIG. 7 corresponds to the operation S210 of FIG. 6, and will not be described in detail below.

Referring to FIG. 7, the computing device 100 according to the exemplary embodiment of the present disclosure may identify a color space of the medical image 41 that includes a region of interest detected through a deep learning model (S320). The computing device 100 may perform different computational operations based on the color space of the medical image 41 identified through the operation S320 to determine a contour color (S380). For example, the computing device 100 may identify whether the color space of the medical image 41 is an RGB space or a grayscale space. When the color space of the medical image 41 is an RGB space, the computing device 100 may determine a contour color of the region of interest through a process of determining candidate color values based on a color distribution in the RGB space. When the color space of the medical image 41 is a gray-scale space, the computing device 100 may determine the contour color of the region of interest based on the color distribution in the gray-scale space in a separate computational process distinct from the case of an RGB space.

Specifically, when the color space of the medical image 41 is an RGB space, the computing device 100 may derive statistical information representing the color distribution on a pixel-by-pixel basis from the medical image 41 to determine the color of the contour. For example, the computing device 100 may generate a histogram representing a pixel-by-pixel color distribution within the RGB space, based on all regions of the medical image 41. The computing device 100 may determine the colors used in the pixels configuring the region of interest included in the medical image 41 through the histogram representing the color distribution on a pixel-by-pixel basis. Additionally, the computing device 100 may determine colors that make the region of interest be clearly distinguished from surrounding areas through a histogram representing the color distribution on a pixel-by-pixel basis.

The computing device 100 may determine a first candidate color value based on the frequency of occurrence of the colors present in the histogram (S330). The computing device 100 may determine the at least one color value that prominently represents a predetermined color as the first candidate color value, based on the at least one color having the lowest frequency of occurrence among the colors present in the histogram. In this case, the predetermined color may be a color that is most visually striking to the human eye against the background of the medical image, or a color that is not used in the region of interest but has a complementary color relationship to a color used in the region of interest. For example, the computing device 100 may recognize the frequency of occurrence of colors present in the histogram. The computing device 100 may recognize the frequency of occurrence of the colors in order of lowest to highest and determine at least one color value that prominently represents yellow, red, or green as a first candidate color value. In other words, the computing device 100 may determine a color value that prominently represents at least one of yellow, red, or green as a first candidate color value based on the frequency of occurrence in the histogram. The computing device 100 may also determine the first candidate color value by reviewing, in order, a yellow-intense color, a red-intense color, and a green-intense color based on the frequency of occurrence in the histogram. That is, the computing device 100 may also determine the first candidate color value by determining whether a yellow-intense color exists among the least frequently occurring colors in the histogram, and, when a yellow-intense color does not exist, sequentially determining a red-intense color and a green-intense color. Thus, the determination of the first candidate color value may be understood to be the determination of the RGB color value at which the contour of the region of interest may be best visually represented. As the yellow color, the red color, and the green color described above with respect to the predetermined colors are only examples, the predetermined color may be varied within the scope understood by those skilled in the art in various considerations of colors and visual emphasis effects expressed in medical images.

The computing device 100 may convert the color space of the medical image 41 to the HSV space, and determine a second candidate color value based on the histogram in the HSV space (S340). The computing device 100 may select an unoccupied hue from the histogram in the HSV space. The computing device 100 may select saturation and a value of brightness at which visual contrast is prominent based on the brightness of the pixels included in a candidate region including the region of interest. The computing device 100 may determine a second candidate color value based on the selected hue, saturation, and value of brightness in the HSV space. For example, the computing device 100 may convert a histogram representing a pixel-by-pixel color distribution in the RGB space to an HSV space. The computing device 100 may select a hue that does not exist on the histogram representing the distribution of colors in the HSV space. Additionally, the computing device 100 may recognize the brightness of the pixels included in the candidate region including the region of interest to select the saturation and the value of brightness that provides the greatest visual contrast effect. In this case, the candidate region includes the region of interest and the surrounding area surrounding the region of interest, and may be twice the size of the region of interest. However, the twice the size of the region of interest is an example, and the present disclosure is not limited thereto. In other words, the computing device 100 may compare the brightness in the HSV space of the pixels included in the region of interest and its surrounding region to determine the saturation and the value of brightness that represent well the contrast effect between the region of interest and the surrounding region. The computing device 100 may determine a second candidate color value including the hue, saturation, and value of brightness derived through the selection process described above. Thus, the determination of the second candidate color value may be understood as the determination of the HSV color value at which the contour of the region of interest may be best visually represented.

The computing device 100 may determine a third candidate color value in the grayscale based on the brightness of the pixels included in the medical image 41 (S350). The computing device 100 may select a color value on a grayscale that exhibits prominent visual contrast based on the brightness of the pixels included in the candidate region including the region of interest. The computing device 100 may determine the selected color value in the grayscale as a third candidate color value. For example, the computing device 100 may select a color value in the grayscale that exhibits the greatest visual contrast effect based on the brightness of the pixels included in the candidate region including the region of interest in the RGB space. The computing device 100 may also convert the RGB space to a grayscale space to select a color value in the grayscale that exhibits the greatest visual contrast effect. In this case, the candidate region includes the region of interest and the surrounding area surrounding the region of interest, and may be twice the size of the region of interest. However, the twice the size of the region of interest is an example, and the present disclosure is not limited thereto. In other words, the computing device 100 may compare the brightness in the RGB or grayscale space of the pixels included in the region of interest and its surrounding region to determine a color value in the grayscale that exhibits a good contrast effect between the region of interest and the surrounding region. The computing device 100 may determine a third candidate color value including the color value of the selected gray scale through the computational process described above. Thus, the determination of the third candidate color value may be understood as the determination of a grayscale color value at which the contour of the region of interest may be best visually represented.

The operations by the computing device 100, represented by the previously described operations S330, S340, and S350, may be performed sequentially, as shown in FIG. 7, or may be performed independently of each other (in parallel).

The computing device 100 may determine a color of the contour marking the region of interest based on the first candidate color value, the second candidate color value, and the third candidate color value (S380). Each candidate color value represents a color value that best represents the contrast effect between the region of interest and surrounding areas in different color spaces. Thus, the colors of the contour based on the first candidate color value, the second candidate color value, and the third candidate color value may consist of colors that best exhibit the contrast effect in any color space. That is, the computing device 100 may configure the color of the contour through the computational operations represented by operations S330, S340, and S350 described above so that the region of interest is distinguishable from its surrounding areas and is well displayed in any color space.

On the other hand, when the color space of the medical image 41 is a grayscale space, the computing device 100 may derive statistical information representing a pixel-by-pixel color distribution from the medical image 41 to determine the color of the contour. For example, the computing device 100 may generate a histogram representing a pixel-by-pixel color distribution within the grayscale space, based on all regions of medical image 41. The computing device 100 may determine the colors used in the pixels configuring the region of interest included in the medical image 41 through the histogram representing the color distribution on a pixel-by-pixel basis. Additionally, the computing device 100 may determine colors that make the region of interest be clearly distinguished from surrounding areas through a histogram representing the color distribution on a pixel-by-pixel basis.

Based on the histogram, the computing device 100 may identify at least one color that does not appear in the region of interest (S370). The computing device 100 may identify the color in the grayscale that does not appear in the histogram among the pixels configuring the region of interest. In other words, the computing device 100 may identify a color in the grayscale that is not used by the region of interest and use the identified color in the grayscale to determine a contour color to visually distinguish the region of interest from surrounding areas.

The computing device 100 may determine a color of the contour marking the region of interest based on at least one color that does not appear in the region of interest (S380). Based on the at least one color that does not appear in the region of interest, the computing device 100 may determine different colors that are distinguishable from each other based on the type and the number of contours that mark the region of interest. For example, when there are multiple regions of interest of each type, it is necessary to differentiate the contour color of the regions of interest according to the type and the number of regions of interest to make an accurate determination. Thus, the computing device 100 may determine the colors of the contours by selecting colors that are distinguishable by the human eye by the type and the number of contours in the region of interest based on at least one color that does not appear per region of interest. Whether the colors are distinguishable by the human eye may be determined based on reference data, such as a color palette that shows color variations that are distinguishable by the human eye. In this way, the computing device 100 may determine contour information 45 associated with the colors that are clearly distinguishable by the human eye, even in the grayscale space, where the representation of contrast between colors is more difficult than in the RGB space.

FIG. 8 is a diagram specifically illustrating a process for determining elements associated with a contour shape of a region of interest included in a medical image of the computing device according to the exemplary embodiment of the present disclosure. When determining the color of the contour in FIG. 7 is a process for accurately visualizing the region of interest detected by the deep learning model, determining the shape of the contour in FIG. 8 may be a process for associating the detection value of the region of interest with the visual representation of the region of interest so that intuitive information is transmitted to the user.

The operation S410 shown in FIG. 8 corresponds to the operation S210 of FIG. 6 and will not be described in detail below.

Referring to FIG. 8, the computing device 100 according to the exemplary embodiment of the present disclosure may determine a representation element associated with the shape of the contour of the region of interest based on the detection information 53 of the region of interest (S450). The computing device 100 may determine the representation elements associated with the shape of the contour in response to the detection information 53 of the region of interest, such that the detection information 53 of the region of interest is reflected in the representation elements associated with the shape of the contour of the region of interest and be intuitively interpreted. In this case, the detection information 53 of the region of interest may include at least one of a probability value 55 regarding the presence of the region of interest and a numerical value 57, such as a size and volume, of the region of interest. Further, the representation element related to the shape of the contour of the region of interest may include at least one of the thickness of the contour, the sharpness of the contour, the precision of the contour, or the sharpness of the shadow of the contour.

Specifically, the computing device 100 may determine a quantitative magnitude (or degree) of the representation element associated with the shape of the contour based on the qualitative magnitude (or degree) of the detection information 53 of the region of interest. In other words, the computing device 100 may determine at least one of the thickness of the contour, the sharpness of the contour, the precision of the contour, and the sharpness of the shadow of the contour, based on the magnitude of at least one of the probability value 55 regarding the presence of the region of interest and the numerical value 57 of the region of interest (S420, S430, and S440). In this case, as the magnitude of at least one of the probability value 55 regarding the presence of the region of interest and the numerical value 57 of the region of interest increases, the magnitude of at least one of the thickness of the contour, the sharpness of the contour, the precision of the contour, and the sharpness of the shadow of the contour may also increase.

For example, the computing device 100 may determine the representation element such that as the probability value regarding the presence of the region of interest increases, the thickness of the contour increases. When the medical image is a three-dimensional image, such as a CT image or MRI image, the computing device 100 may determine a representation element such that as the volume of the region of interest increases, the thickness of the contour increases. When a shadow is displayed on the contour, the computing device 100 may determine a representation element such that as the probability value regarding the presence of the region of interest increases, the sharpness of the shadow increases. Conversely, the computing device 100 may determine the representation element such that as the probability value regarding the presence of the region of interest decreases, the shadow is displayed to be blurry. The computing device 100 may determine the representation element such that as the probability value regarding the presence of the region of interest increases, the contour itself is displayed more sharply. Conversely, the computing device 100 may determine the representation element such that as the probability value regarding the presence of the region of interest decreases, the contour itself is displayed more blurry. The computing device 100 may determine the representation element such that as the probability value regarding the presence of the region of interest increases, the contour itself is displayed more precisely. The display of the contour itself precisely means configuring the contour with many points to make the contour appear smooth, like a curve. Conversely, the computing device 100 may determine the representation element such that the contour itself regarding the presence of the region of interest is displayed rough. The display of the contour itself to be rough means configuring the contour with fewer points so that the contour looks like a polygon. The processing process allows the user to see the quantitative magnitude (or degree) of the representation elements associated with the shape of the contour and intuitively interpret the detection result for the region of interest.

On the other hand, referring to FIG. 8, when the probability value 55 is to be displayed along with the contour information 59, the computing device 100 may determine a representation element associated with the letter representing the probability value 55 based on a quantitative numerical value of the probability value 55. For example, the computing device 100 may determine a representation element such that as the probability value regarding the presence of the region of interest increases, the size of the letters representing the probability value is displayed larger. Conversely, the computing device 100 may determine a representation element such that as the probability value regarding the presence of the region of interest decreases, the size of the letters representing the probability value is displayed smaller.

FIG. 9 is a flowchart illustrating a medical image processing method according to another exemplary embodiment of the present disclosure. The computing device performing the computational processes described with reference to FIGS. 4 to 8 is distinguished from a computing device performing the computational processes illustrated in FIG. 9. Referring to FIG. 2, it can be understood that the device performing the computations of FIGS. 4 to 8 corresponds to the first computing device 310, and the device performing the computations of FIG. 9 corresponds to the second computing device 350. Accordingly, the present disclosure will be described while distinguishing the computing devices based on FIG. 2.

Referring to FIG. 9, in operation S510, a second computing device 350 according to another exemplary embodiment of the present disclosure may receive format information defining elements that determine the representation of a medical image. In this case, the format information may be generated through an operation of a first computing device 310. Specifically, the format information may be generated based on contour information about regions of interest in the medical image detected by using a pre-trained deep learning model. The second computing device 350 may receive, through wired or wireless communication with the first computing device 310, format information defining representational elements regarding contour colors and shape of the region of interest.

In operation S520, the second computing device 350 may combine the medical image and the format information corresponding to the medical image to visualize a result of the analysis for the region of interest. Since the format information defines a location of an image in which the visual elements of the region of interest are to be represented, the second computing device 350 may determine a medical image corresponding to the format information received in operation S510, and may combine the determined medical image with the format information to generate an image in which the region of interest is represented. In this case, the medical image combined with the format information may be an original image analyzed by the first computing device 310, or may be a medical image that has been previously obtained and stored by the second computing device 350.

In operation S530, the second computing device 350 may generate a user interface that reflects the result of the combination of the format information and the medical image. The user interface may include a layer for outputting an image representing the color and shape of the contour of the region of interest, may also include all of a layer for user input, a layer for outputting numerical information related to the region of interest, and the like. On the other hand, the second computing device 350 may output the image generated as a result of the combination of the format information and the medical image through an output unit as it is and provide the generated image to the user. The second computing device 350 may also provide the image generated as the result of the combination of the format information and the medical image to a separate output terminal.

FIG. 10 is a simple and general schematic diagram illustrating an example of a computing environment in which the embodiments of the present disclosure are implementable.

The present disclosure has been described as being generally implementable by the computing device, but those skilled in the art will appreciate well that the present disclosure is combined with computer executable commands and/or other program modules executable in one or more computers and/or be implemented by a combination of hardware and software.

In general, a program module includes a routine, a program, a component, a data structure, and the like performing a specific task or implementing a specific abstract data form. Further, those skilled in the art will well appreciate that the method of the present disclosure may be carried out by a personal computer, a hand-held computing device, a microprocessor-based or programmable home appliance (each of which may be connected with one or more relevant devices and be operated), and other computer system configurations, as well as a single-processor or multiprocessor computer system, a mini computer, and a main frame computer.

The embodiments of the present disclosure may be carried out in a distribution computing environment, in which certain tasks are performed by remote processing devices connected through a communication network. In the distribution computing environment, a program module may be located in both a local memory storage device and a remote memory storage device.

The computer generally includes various computer readable media. The computer accessible medium may be any type of computer readable medium, and the computer readable medium includes volatile and non-volatile media, transitory and non-transitory media, and portable and non-portable media. As a non-limited example, the computer readable medium may include a computer readable storage medium and a computer readable transport medium. The computer readable storage medium includes volatile and non-volatile media, transitory and non-transitory media, and portable and non-portable media constructed by a predetermined method or technology, which stores information, such as a computer readable command, a data structure, a program module, or other data. The computer readable storage medium includes a RAM, a Read Only Memory (ROM), an Electrically Erasable and Programmable ROM (EEPROM), a flash memory, or other memory technologies, a Compact Disc (CD)-ROM, a Digital Video Disk (DVD), or other optical disk storage devices, a magnetic cassette, a magnetic tape, a magnetic disk storage device, or other magnetic storage device, or other predetermined media, which are accessible by a computer and are used for storing desired information, but is not limited thereto.

The computer readable transport medium generally implements a computer readable command, a data structure, a program module, or other data in a modulated data signal, such as a carrier wave or other transport mechanisms, and includes all of the information transport media. The modulated data signal means a signal, of which one or more of the characteristics are set or changed so as to encode information within the signal. As a non-limited example, the computer readable transport medium includes a wired medium, such as a wired network or a direct-wired connection, and a wireless medium, such as sound, Radio Frequency (RF), infrared rays, and other wireless media. A combination of the predetermined media among the foregoing media is also included in a range of the computer readable transport medium.

An illustrative environment 1100 including a computer 1102 and implementing several aspects of the present disclosure is illustrated, and the computer 1102 includes a processing device 1104, a system memory 1106, and a system bus 1108. The system bus 1108 connects system components including the system memory 1106 (not limited) to the processing device 1104. The processing device 1104 may be a predetermined processor among various commonly used processors. A dual processor and other multi-processor architectures may also be used as the processing device 1104.

The system bus 1108 may be a predetermined one among several types of bus structure, which may be additionally connectable to a local bus using a predetermined one among a memory bus, a peripheral device bus, and various common bus architectures. The system memory 1106 includes a ROM 1110, and a RAM 1112. A basic input/output system (BIOS) is stored in a non-volatile memory 1110, such as a ROM, an EPROM, and an EEPROM, and the BIOS includes a basic routing helping a transport of information among the constituent elements within the computer 1102 at a time, such as starting. The RAM 1112 may also include a high-rate RAM, such as a static RAM, for caching data.

The computer 1102 also includes an embedded hard disk drive (HDD) 1114 (for example, enhanced integrated drive electronics (EIDE) and serial advanced technology attachment (SATA))—the embedded HDD 1114 being configured for exterior mounted usage within a proper chassis (not illustrated)—a magnetic floppy disk drive (FDD) 1116 (for example, which is for reading data from a portable diskette 1118 or recording data in the portable diskette 1118), and an optical disk drive 1120 (for example, which is for reading a CD-ROM disk 1122, or reading data from other high-capacity optical media, such as a DVD, or recording data in the high-capacity optical media). A hard disk drive 1114, a magnetic disk drive 1116, and an optical disk drive 1120 may be connected to a system bus 1108 by a hard disk drive interface 1124, a magnetic disk drive interface 1126, and an optical drive interface 1128, respectively. An interface 1124 for implementing an outer mounted drive includes, for example, at least one of or both a universal serial bus (USB) and the Institute of Electrical and Electronics Engineers (IEEE) 1394 interface technology.

The drives and the computer readable media associated with the drives provide non-volatile storage of data, data structures, computer executable commands, and the like. In the case of the computer 1102, the drive and the medium correspond to the storage of random data in an appropriate digital form. In the description of the computer readable media, the HDD, the portable magnetic disk, and the portable optical media, such as a CD, or a DVD, are mentioned, but those skilled in the art will well appreciate that other types of computer readable media, such as a zip drive, a magnetic cassette, a flash memory card, and a cartridge, may also be used in the illustrative operation environment, and the predetermined medium may include computer executable commands for performing the methods of the present disclosure.

A plurality of program modules including an operation system 1130, one or more application programs 1132, other program modules 1134, and program data 1136 may be stored in the drive and the RAM 1112. An entirety or a part of the operation system, the application, the module, and/or data may also be cached in the RAM 1112. It will be well appreciated that the present disclosure may be implemented by several commercially usable operation systems or a combination of operation systems.

A user may input a command and information to the computer 1102 through one or more wired/wireless input devices, for example, a keyboard 1138 and a pointing device, such as a mouse 1140. Other input devices (not illustrated) may be a microphone, an IR remote controller, a joystick, a game pad, a stylus pen, a touch screen, and the like. The foregoing and other input devices are frequently connected to the processing device 1104 through an input device interface 1142 connected to the system bus 1108, but may be connected by other interfaces, such as a parallel port, an IEEE 1394 serial port, a game port, a USB port, an IR interface, and other interfaces.

A monitor 1144 or other types of display devices are also connected to the system bus 1108 through an interface, such as a video adaptor 1146. In addition to the monitor 1144, the computer generally includes other peripheral output devices (not illustrated), such as a speaker and a printer.

The computer 1102 may be operated in a networked environment by using a logical connection to one or more remote computers, such as remote computer(s) 1148, through wired and/or wireless communication. The remote computer(s) 1148 may be a work station, a computing device computer, a router, a personal computer, a portable computer, a microprocessor-based entertainment device, a peer device, and other general network nodes, and generally includes some or an entirety of the constituent elements described for the computer 1102, but only a memory storage device 1150 is illustrated for simplicity. The illustrated logical connection includes a wired/wireless connection to a local area network (LAN) 1152 and/or a larger network, for example, a wide area network (WAN) 1154. The LAN and WAN networking environments are general in an office and a company, and make an enterprise-wide computer network, such as an Intranet, easy, and all of the LAN and WAN networking environments may be connected to a worldwide computer network, for example, the Internet.

When the computer 1102 is used in the LAN networking environment, the computer 1102 is connected to the local network 1152 through a wired and/or wireless communication network interface or an adaptor 1156. The adaptor 1156 may make wired or wireless communication to the LAN 1152 easy, and the LAN 1152 also includes a wireless access point installed therein for the communication with the wireless adaptor 1156. When the computer 1102 is used in the WAN networking environment, the computer 1102 may include a modem 1158, is connected to a communication computing device on a WAN 1154, or includes other means setting communication through the WAN 1154 via the Internet. The modem 1158, which may be an embedded or outer-mounted and wired or wireless device, is connected to the system bus 1108 through a serial port interface 1142. In the networked environment, the program modules described for the computer 1102 or some of the program modules may be stored in a remote memory/storage device 1150. The illustrated network connection is illustrative, and those skilled in the art will appreciate well that other means setting a communication link between the computers may be used.

The computer 1102 performs an operation of communicating with a predetermined wireless device or entity, for example, a printer, a scanner, a desktop and/or portable computer, a portable data assistant (PDA), a communication satellite, predetermined equipment or place related to a wirelessly detectable tag, and a telephone, which is disposed by wireless communication and is operated. The operation includes a wireless fidelity (Wi-Fi) and Bluetooth wireless technology at least. Accordingly, the communication may have a pre-defined structure, such as a network in the related art, or may be simply ad hoc communication between at least two devices.

The Wi-Fi enables a connection to the Internet and the like even without a wire. The Wi-Fi is a wireless technology, such as a cellular phone, which enables the device, for example, the computer, to transmit and receive data indoors and outdoors, that is, in any place within a communication range of a base station. A Wi-Fi network uses a wireless technology, which is called IEEE 802.11 (a, b, g, etc.) for providing a safe, reliable, and high-rate wireless connection. The Wi-Fi may be used for connecting the computer to the computer, the Internet, and the wired network (IEEE 802.3 or Ethernet is used). The Wi-Fi network may be operated at, for example, a data rate of 11 Mbps (802.11a) or 54 Mbps (802.11b) in an unauthorized 2.4 and 5 GHz wireless band, or may be operated in a product including both bands (dual bands).

Those skilled in the art may appreciate that information and signals may be expressed by using predetermined various different technologies and techniques. For example, data, indications, commands, information, signals, bits, symbols, and chips referable in the foregoing description may be expressed with voltages, currents, electromagnetic waves, magnetic fields or particles, optical fields or particles, or a predetermined combination thereof.

Those skilled in the art will appreciate that the various illustrative logical blocks, modules, processors, means, circuits, and algorithm operations described in relationship to the embodiments disclosed herein may be implemented by electronic hardware (for convenience, called "software" herein), various forms of program or design code, or a combination thereof. In order to clearly describe compatibility of the hardware and the software, various illustrative components, blocks, modules, circuits, and operations are generally illustrated above in relation to the functions of the hardware and the software. Whether the function is implemented as hardware or software depends on design limits given to a specific application or an entire system. Those skilled in the art may perform the function described by various schemes for each specific application, but it shall not be construed that the determinations of the performance depart from the scope of the present disclosure.

Various embodiments presented herein may be implemented by a method, a device, or a manufactured article using a standard programming and/or engineering technology. A term "manufactured article" includes a computer program, a carrier, or a medium accessible from a predetermined computer-readable storage device. For example, the computer-readable storage medium includes a magnetic storage device (for example, a hard disk, a floppy disk, and a magnetic strip), an optical disk (for example, a CD and a DVD), a smart card, and a flash memory device (for example, an EEPROM, a card, a stick, and a key drive), but is not limited thereto. Further, various storage media presented herein include one or more devices and/or other machine-readable media for storing information.

It shall be understood that a specific order or a hierarchical structure of the operations included in the presented processes is an example of illustrative accesses. It shall be understood that a specific order or a hierarchical structure of the operations included in the processes may be rearranged within the scope of the present disclosure based on design priorities. The accompanying method claims provide various operations of elements in a sample order, but it does not mean that the claims are limited to the presented specific order or hierarchical structure.

The description of the presented embodiments is provided so as for those skilled in the art to use or carry out the present disclosure. Various modifications of the embodiments may be apparent to those skilled in the art, and general principles defined herein may be applied to other embodiments without departing from the scope of the present disclosure. Accordingly, the present disclosure is not limited to the embodiments suggested herein, and shall be interpreted within the broadest meaning range consistent to the principles and new characteristics presented herein.

Mode for Carrying Out the Disclosure

As the described above, the relevant contents are described in the best mode for implementing the present disclosure.

INDUSTRIAL APPLICABILITY

The present disclosure may be used in a computing device and the like for processing a medical image.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A medical image processing method performed by a computing device including at least one processor, the method comprising:

detecting a region of interest in a medical image by using a pre-trained deep learning model;

determining contour information for the region of interest; and generating, based on the contour information, format information defining elements that determine representation of the medical image, wherein the determining of the contour information for the region of interest includes:

identifying a color space of the medical image; and determining a color of a contour marking the region of interest, based on correlation between colors in a color distribution of the region of interest in the medical image of which the color space is identified.

2. The method of claim 1, wherein when the identified color space is an RGB space, the determining of the color of the contour marking the region of interest includes:

deriving a histogram representing a pixel-by-pixel color distribution from the medical image;

determining a first candidate color value based on a frequency of occurrence of colors present in the histogram;

transforming the color space of the medical image into a Hue Saturation Value (HSV) space, and determining a second candidate color value based on the histogram in the HSV space;

determining a third candidate color value in a grayscale based on brightness of pixels included in the medical image; and determining the color of the contour marking the region of interest based on the first candidate color value, the second candidate color value, and the third candidate color value.

3. The method of claim 2, wherein the determining of the first candidate color value based on the frequency of occurrence of the colors present in the histogram includes determining, based on at least one color having a lowest frequency of occurrence among the colors present in the histogram, at least one color value that prominently represents a predetermined color as the first candidate color value.

4. The method of claim 2, wherein the determining of the second candidate color value based on the histogram in the HSV space includes:

selecting an unoccupied hue from the histogram in the HSV space;

selecting saturation and a value of brightness at which visual contrast is prominent based on brightness of pixels included in a candidate region including the region of interest; and determining the second candidate color value based on the selected hue, saturation, and value of brightness.

5. The method of claim 2, wherein the determining of the third candidate color value based on the brightness of the pixels included in the medical image includes:

based on the brightness of the pixels included in a candidate region including the region of interest, selecting a color value in a grayscale at which visual contrast is prominent; and determining the selected color value in the grayscale as the third candidate color value.

6. The method of claim 1, wherein when the identified color space is a grayscale space, the determining of the color of the contour marking the region of interest includes:

deriving a histogram representing a pixel-by-pixel color distribution from the medical image;

identifying at least one color not appearing in the region of interest based on the histogram; and determining, based on the at least one color not appearing in the region of interest, the color of the contour marking the region of interest.

7. The method of claim 6, wherein the determining of, based on the at least one color not appearing in the region of interest, the color of the contour marking the region of interest includes determining, based on the at least one color not appearing in the region of interest, colors that are distinguishable from each other in accordance with a type and the number of contours that mark the region of interest.

8. The method of claim 1, wherein the determining of the contour information for the region of interest includes determining a representation element related to a shape of the contour of the region of interest based on detection information of the region of interest.

9. The method of claim 8, wherein the detection information includes at least one of a probability value regarding presence of the region of interest or a numerical value of the region of interest, and wherein the representation element related to the shape of the contour of the region of interest includes at least one of a thickness of the contour, sharpness of the contour, precision of the contour, or sharpness of a shadow of the contour.

10. The method of claim 8, wherein the determining of the representation element related to the shape of the contour of the region of interest based on the detection information of the region of interest includes determining at least one of a thickness of the contour, sharpness of the contour, precision of the contour, or sharpness of a shadow of the contour, based on a magnitude of at least one of a probability value regarding presence of the region of interest or a numerical value of the region of interest.

11. The method of claim 10, wherein as the magnitude of at least one of the probability value regarding the presence of the region of interest or the numerical value of the region of interest increases, a magnitude of at least one of the thickness of the contour, the sharpness of the contour, the precision of the contour, or the sharpness of the shadow of the contour increases.

12. A medical image processing method performed by a computing device including at least one processor, the method comprising:

receiving format information defining elements that determine representation of a medical image;

combining the medical image with format information corresponding to the medical image; and generating a user interface reflecting a result of the combination, wherein the format information is generated based on contour information for a region of interest of the medical image detected using a pre-trained deep learning model, wherein the determining of the contour information for the region of interest includes:

identifying a color space of the medical image; and determining a color of a contour marking the region of interest, based on correlation between colors in a color distribution of the region of interest in the medical image of which the color space is identified.

13. A computing device for processing a medical image, the computing device comprising:

a processor including at least one core;

a memory including program codes executed in the processor; and a network unit for receiving a medical image, wherein the processor:

detects a region of interest in the medical image by using a pre-trained deep learning model, determines contour information for the region of interest, and generates, based on the contour information, format information defining elements that determine a representation layer of the medical image, wherein the determining of the contour information for the region of interest includes:

identifying a color space of the medical image; and determining a color of a contour marking the region of interest, based on correlation between colors in a color distribution of the region of interest in the medical image of which the color space is identified.

14. The computing device of claim 13, wherein when the identified color space is an RGB space, the determining of the color of the contour marking the region of interest includes:

deriving a histogram representing a pixel-by-pixel color distribution from the medical image;

determining a first candidate color value based on a frequency of occurrence of colors present in the histogram;

transforming the color space of the medical image into a Hue Saturation Value (HSV) space, and determining a second candidate color value based on the histogram in the HSV space;

determining a third candidate color value in a grayscale based on brightness of pixels included in the medical image; and determining the color of the contour marking the region of interest based on the first candidate color value, the second candidate color value, and the third candidate color value.

15. The computing device of claim 14, wherein the determining of the first candidate color value based on the frequency of occurrence of the colors present in the histogram includes determining, based on at least one color having a lowest frequency of occurrence among the colors present in the histogram, at least one color value that prominently represents a predetermined color as the first candidate color value.

16. The computing device of claim 14, wherein the determining of the second candidate color value based on the histogram in the HSV space includes:

selecting an unoccupied hue from the histogram in the HSV space;

selecting saturation and a value of brightness at which visual contrast is prominent based on brightness of pixels included in a candidate region including the region of interest; and determining the second candidate color value based on the selected hue, saturation, and value of brightness.

17. The computing device of claim 14, wherein the determining of the third candidate color value based on the brightness of the pixels included in the medical image includes:

based on the brightness of the pixels included in a candidate region including the region of interest, selecting a color value in a grayscale at which visual contrast is prominent; and determining the selected color value in the grayscale as the third candidate color value.

18. The computing device of claim 13, wherein when the identified color space is a grayscale space, the determining of the color of the contour marking the region of interest includes:

deriving a histogram representing a pixel-by-pixel color distribution from the medical image;

identifying at least one color not appearing in the region of interest based on the histogram; and determining, based on the at least one color not appearing in the region of interest, the color of the contour marking the region of interest.

19. The computing device of claim 18, wherein the determining of, based on the at least one color not appearing in the region of interest, the color of the contour marking the region of interest includes determining, based on the at least one color not appearing in the region of interest, colors that are distinguishable from each other in accordance with a type and the number of contours that mark the region of interest.

20. The computing device of claim 13, wherein the determining of the contour information for the region of interest includes determining a representation element related to a shape of the contour of the region of interest based on detection information of the region of interest.

* * * * *